(12) United States Patent
Baynham et al.

(10) Patent No.: US 7,211,112 B2
(45) Date of Patent: May 1, 2007

(54) SPINAL FUSION DEVICE

(75) Inventors: Bret O. Baynham, Jupiter, FL (US); G. Clay Baynham, Jupiter, FL (US); Matthew G. Baynham, Jupiter, FL (US); David R. Campbell, Jupiter, FL (US)

(73) Assignee: Atlas Spine, Jupiter, FL (US)

( * ) Notice: Subject to any disclaimer, the term of this patent is extended or adjusted under 35 U.S.C. 154(b) by 516 days.

(21) Appl. No.: 10/776,663

(22) Filed: Feb. 10, 2004

(65) Prior Publication Data
US 2005/0177235 A1    Aug. 11, 2005

(51) Int. Cl.
*A61F 2/44* (2006.01)
*A61F 2/30* (2006.01)

(52) U.S. Cl. .................. 623/17.11; 623/17.15

(58) Field of Classification Search .. 623/17.11–17.16; 606/61
See application file for complete search history.

(56) References Cited

U.S. PATENT DOCUMENTS

| 5,609,635 | A |   | 3/1997 | Michelson |
| 5,658,335 | A |   | 8/1997 | Allen |
| 5,665,122 | A | * | 9/1997 | Kambin .................... 623/17.16 |
| 5,865,848 | A | * | 2/1999 | Baker ....................... 623/17.15 |
| 6,015,436 | A |   | 1/2000 | Schonhoffer |
| 6,120,506 | A |   | 9/2000 | Kohrs et al. |
| 6,562,074 | B2 |  | 5/2003 | Gerbec et al. |
| 6,706,070 | B1 |  | 3/2004 | Wagner et al. |
| 6,733,535 | B2 |  | 5/2004 | Michelson |
| 2004/0087947 | A1 | | 5/2004 | Lim et al. |

* cited by examiner

Primary Examiner—Pedro Philogene
(74) Attorney, Agent, or Firm—McHale & Slavin P.A.

(57) ABSTRACT

A spinal fusion device for implantation between adjacent vertebrae is formed in the approximate shape of a hollow cube. The device has an upper section and a lower section relatively movable with regard to each other. The sidewalls of the upper section and the lower section terminate in complementary inclined planes so that as the sections move away from each other the height of the device lessens and as the sections move toward each other the height of the device increases. A distractor is placed within the hollow body and contacts the upper and lower sections by a link which is used to adjust the height of the device.

10 Claims, 3 Drawing Sheets

SPINAL FUSION DEVICE

FIELD OF THE INVENTION

This invention relates to the field of orthopedic and neuro-surgery and, more particularly, to implants to be placed between vertebrae in the spine.

BACKGROUND OF THE INVENTION

Spinal stabilization is one approach to alleviating chronic back pain caused by displaced disk material or excessive movement of individual vertebrae. Conventional stabilization techniques include fusing two or more vertebrae together to circumvent or immobilize the area of excessive movement. Normally, the vertebral disk material which separates the vertebrae is removed and bone graft material is inserted in the space for interbody fusion. In addition to or, in place of, the bone graft material, a spinal implant may be inserted in the intervertebral space.

The conventional surgical approach for stabilization has been posteriorly for ease of access to the spine and to avoid interfering with internal organs and tissue. Usually the implant site is prepared to maintain natural lordosis and to accept a certain sized implant within certain pressure limits. This requires considerable time and skill by the surgeon.

DESCRIPTION OF THE PRIOR ART

U.S. Pat. No. 6,562,074 to Gerber et al issued May 13, 2003 discloses a spinal insert which can be manipulated to adjust the height of the implant through links connected to the upper and lower plates.

U.S. Pat. No. 6,120,506 issued Sep. 19, 2000 to Kohrs et al discloses a lordotic implant and a tap for use in preparing the vertebrae. The implant is designed to be inserted between the non-parallel end plates of adjacent vertebrae and maintain the natural lordotic angle of the spine. This is done through the use of a threaded tapered plug inserted in a tapped hole in the direction required by the lordosis of the spine. The implant is hollow and has radial apertures for accommodating bone graft material.

U.S. Pat. No. 6,015,436 issued Jan. 18, 2000 to Shoenhoeffer discloses a tubular spinal implant. The implant is hollow and has radial apertures for interbody fusion through bone growth material. The device is placed between adjacent vertebrae with the opposite ends of the tube contacting the opposing vertebrae. The opposite ends are threaded together to form the hollow tube.

SUMMARY OF THE INVENTION

The spinal fusion device is particularly suited for posterior lumbar implantation. The implant has a main body having upper and a lower sections with mating sidewalls relatively movable along an inclined ramp. The sections form a hollow cube-shaped structure with a common open side. The main body is inserted in an extended thin mode between adjacent vertebrae and a distractor is inserted through the common open side. The distractor is connected to one of the sections by a link which causes one section to move along the inclined ramp of the other section for increasing the height of the implant and engaging the opposing surfaces of adjacent vertebrae. The adjacent vertebrae are forced apart as the height of the implant increases. The spinal fusion device may be used unilaterally or bilaterally.

Accordingly, it is an objective of the instant invention to teach a posterior surgical approach for placement of an adjustable spinal implant for interbody fusion allowing the implant to be inserted through a small incision and increased in size in situ.

It is another objective of the instant invention to teach a spinal implant which allows the surgeon to provide for lordosis intraoperatively and to distract through the implant.

It is a further objective of the instant invention to teach a spinal implant having increased contact area in the disk space.

It is yet another objective of the instant invention to teach an implant facilitating interbody fusion through bone graft or an ingrowth-type implant.

Other objectives and advantages of this invention will become apparent from the following description taken in conjunction with the accompanying drawings wherein are set forth, by way of illustration and example, certain embodiments of this invention. The drawings constitute a part of this specification and include exemplary embodiments of the present invention and illustrate various objects and features thereof.

DETAILED DESCRIPTION OF THE INVENTION

Figure 1:
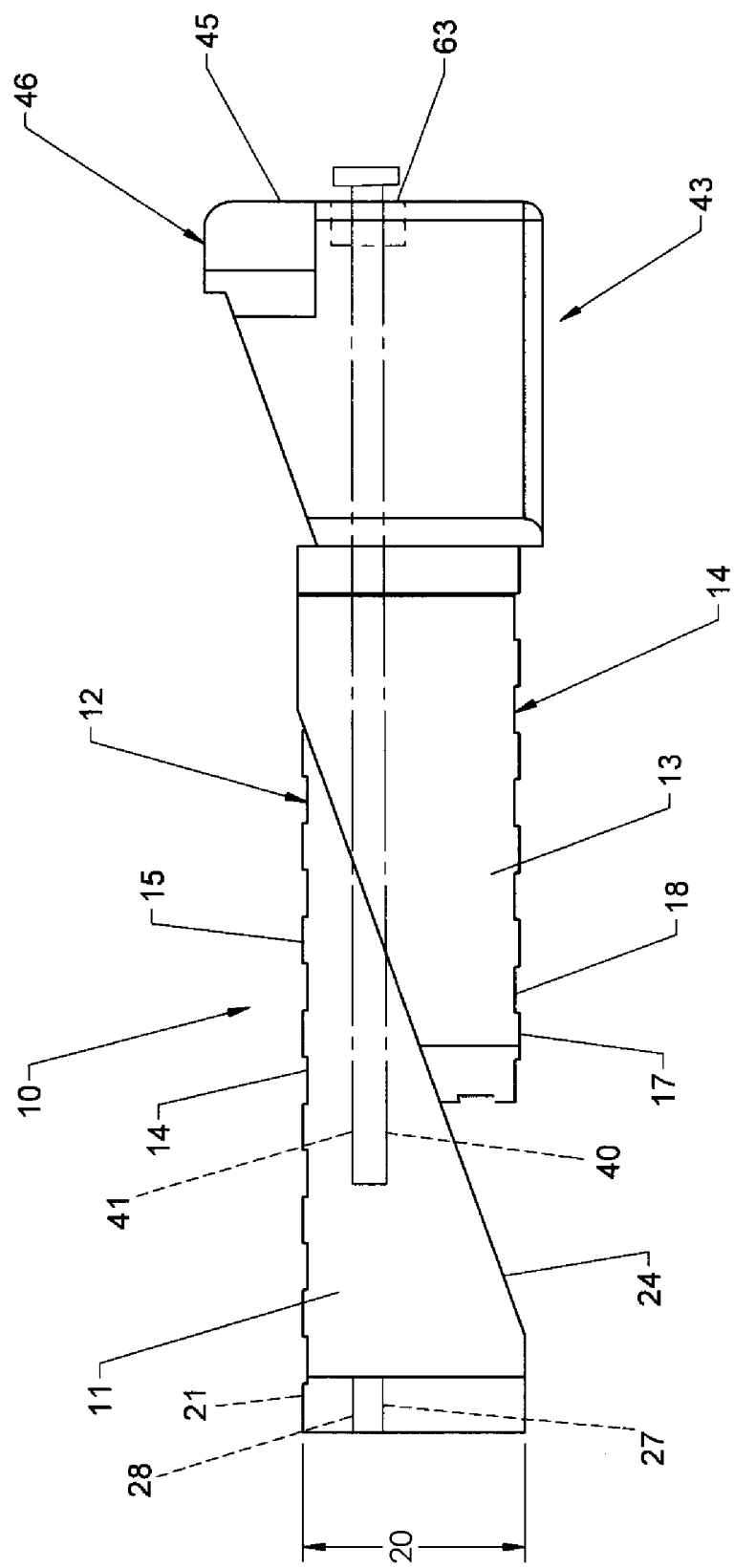
FIG. 1 is a side view of the spinal fusion implant of this invention in the insertion mode.

The spinal fusion device 10 is inserted in the intervertebral space in the insertion mode, shown in FIG. 1, to replace damaged, missing or excised disk material. This extended position allows the implant to be inserted in a small intervertebral space without the necessity of excising structurally sound bone. The upper section 11 has a top surface 12 for engaging the end plate of a vertebra and the lower section 13 has a bottom surface 14 for engaging the end plate of an adjacent vertebra. The top surface 12 and the bottom surface 14 are planar to provide a large contact area with each vertebra. Each contact surface has a roughened finish to provide better purchase on the end plates of the vertebrae. As shown, the top and bottom surfaces have a series of lands and grooves 15, 16, 17 and 18 though other stippled treatment may be employed. Of course, the device may be rotated about its longitudinal axis 180 degrees so that the upper section becomes the lower section and vice versa.

The device 10 has two extreme positions and is adjustable infinitely between those positions, eg., in the insertion mode the extended position of the structure has a height 20 approximately the same as the height of one of the sections and a length approximately twice the length of one section, as shown in FIG. 1. In the increased height mode, the expanded position, shown in FIG. 2, the height 19 is the sum of the height of the individual sections and the length is approximately the same as the length of a section.

The fusion device 10 may be made of conventional materials used for surgical implants, such as stainless steel and its many different alloys, titanium, and any other metal with the requisite strength and biologically inert properties.

Polymeric materials with adequate strength and biological properties may also be used in the construction of the fusion device.

The upper section 11 is formed with an end wall 21 a top surface 12 and depending sidewalls 22 and 23. The sidewalls terminate in an inclined plane 24 which extends from the end wall 21 to the top surface 12. The top surface 12 has a large aperture 25 therethrough to provide for bone ingrowth. The top surface 12 has a narrower flange 26 extending beyond the sidewalls 22 and 23. The flange 26 engages the end wall of the lower section 13 to guide the relative movement of the sections maintaining the upstanding sidewalls and the depending sidewalls in alignment. The end wall 21 has a bore 27 with internal threads 28 to cooperate with the threads 41 on the link 40. The bore may be a blind bore or extend through the end wall 21.

Figure 4:
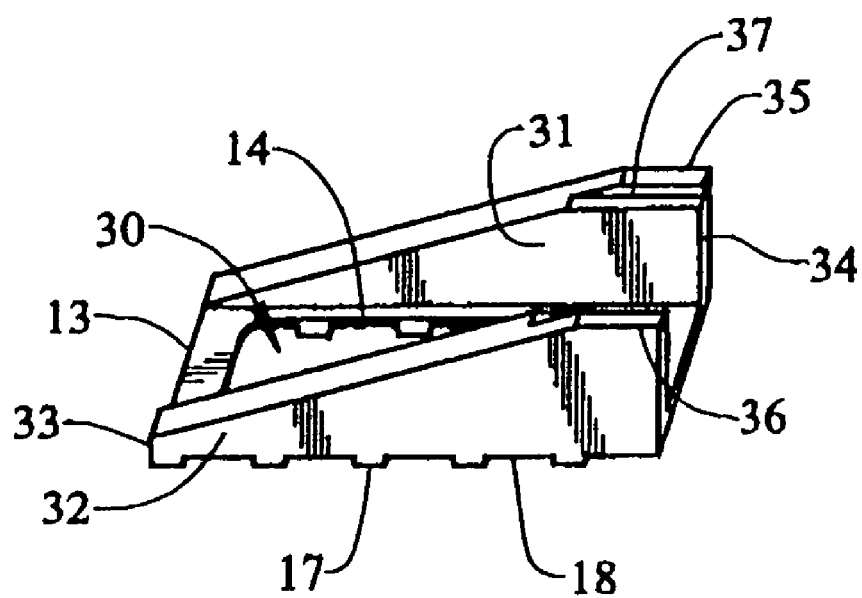
FIG. 4 is a perspective view of the lower section of the implant.

The bottom surface 14 of the lower section 13 has a large aperture 30, as shown in FIG. 4, to facilitate bone ingrowth after implantation. The lower section 13 is a U-shaped channel with opposed upstanding sidewalls 31 and 32 projecting from the bottom surface. The side walls 31 and 32 have a short end 33 and a long end 34. The sidewalls 31 and 32 terminate in an inclined plane extending from the short end 33 toward the long end 34. The upstanding walls each have a vertical extension 35 and 36 beyond the end of the inclined plane. A reduced thickness 37 is formed in the vertical extensions 35 and 36 to accommodate the flange 26 as the upper and lower sections move relative to each other. The movement of the flange through the reduced thickness contributes to the alignment of the upper and lower sections as they move relative to each other.

The ends of the inclined planes of the upstanding and depending walls are smooth ramps to provide ease in the relative sliding contact between the surfaces. Other embodiments of the complementary surfaces may provide additional or substitute guidance to maintain the upper and lower sections in alignment during movement of the contacting surfaces of the inclined planes, such as, the ends of the inclined planes may be sloped across the thickness of the side walls or a stepped ramp may be used.

Figure 2:
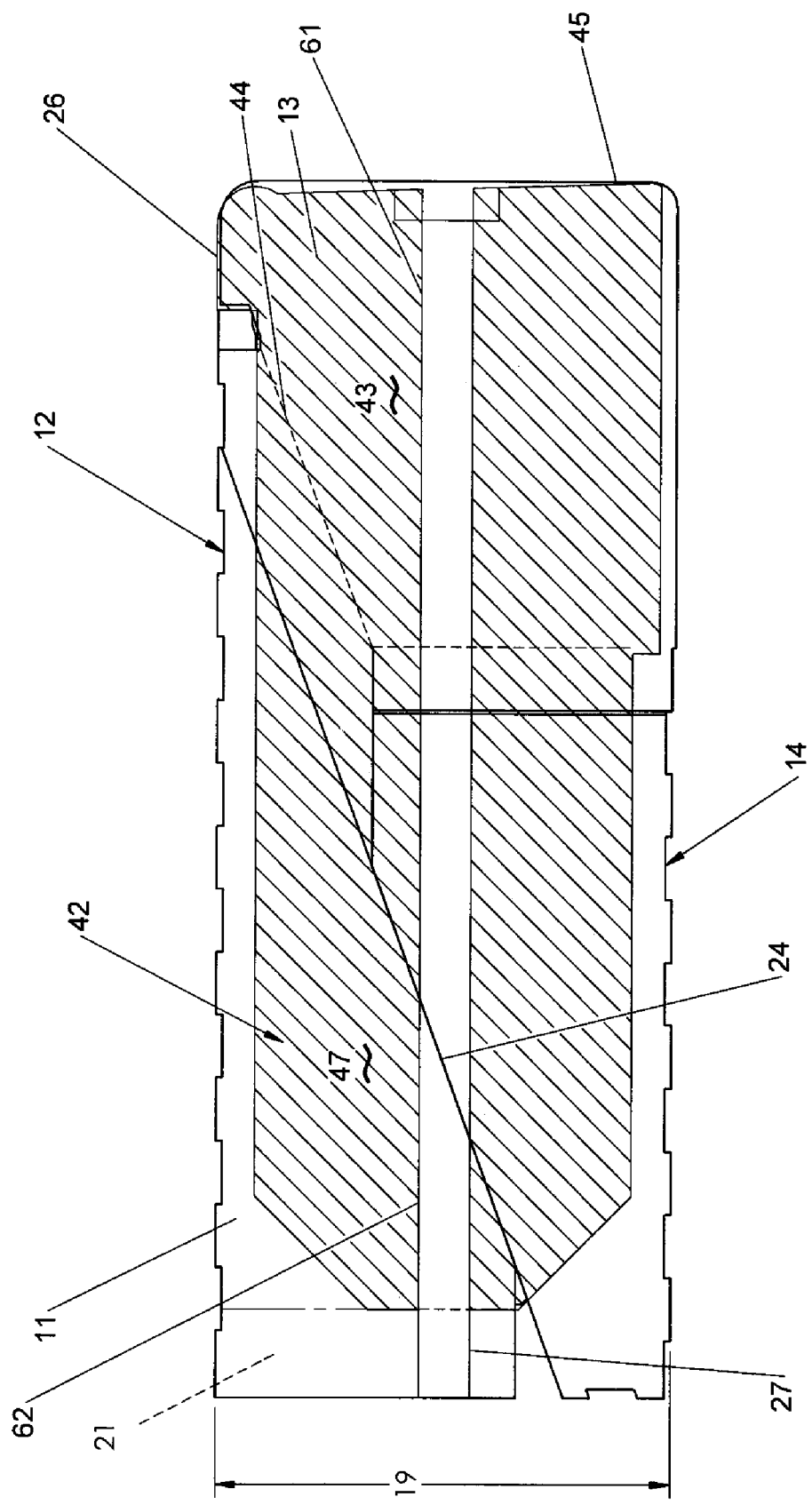
FIG. 2 is a side view of the spinal fusion device in the increased height mode.
Figure 3:
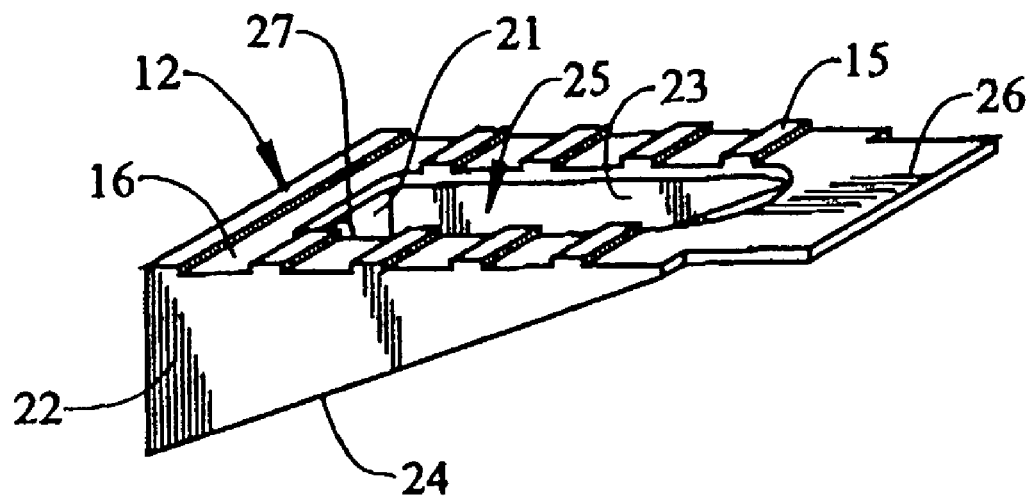
FIG. 3 is a perspective view of the upper section of the implant.

A distractor 42 is shown in FIG. 2. The distractor 42 is dimensioned to be inserted into the interior cavity between the upper section and the lower section of the spinal infusion device 10, as shown in FIG. 1. A plug 43 is dimensioned to be inserted and closes the opening formed in the lower section by the upstanding sidewalls 31, 32 (FIG. 4). The upper surface of the plug has an inclined ramp 44 on each side (only one side shown in FIG. 2) to accommodate the inclined plane 24 of the depending walls 22 and 23 of the upper section. The plug 43 has a larger circumferential end plate 45 dimensioned to extend to the outer periphery of the upper and lower sections to make a smooth outer surface. The upper portion 46 of the end plate 45 engages the end of the flange 26 to act as a stop for relative movement. Extending from the end plug into the cavity of the hollow structure 10 is the body 47 of the distractor 42. The body is connected to the end plug by two rails (not shown) leaving a central area open for bone ingrowth. The end plug 43 and the body 47 each have a bore 61 and 62, respectively. These bores are aligned with the bore 27 in the end wall of the upper section 11, as shown in FIG. 2. The bore 61 has a larger countersunk bore 63 in the end plate 45 (FIG. 1).

As shown in FIG. 1, the spinal fusion device is inserted in the disk space between adjacent vertebrae in the extended position with the top surface in contact with the end plate of one vertebra and the bottom surface in contact with the end plate of an adjacent vertebra. A link 40 traverses the bores 61, 62 and is threaded in bore 27. The surgeon turns the link 40 causing the upper and lower sections to move along the complementary inclined plane to shorten the fusion device and increase the distance between the end plates of the adjacent vertebrae. The adjustment may continue until the flange 26 contacts the end plate 46. At this time, the link may be removed and replaced by a bolt of sufficient length to tighten the upper and lower sections together. While a threaded link and bore are illustrated for adjusting the device, other mechanisms may be used for generating the force to move the sections. For example, a pneumatic, hydraulic or mechanical puller may be used against the end plate to apply linear force to the link rather than torque. And the end wall may have a nipple rather than a bore.

A number of embodiments of the present invention have been described. Nevertheless, it will be understood that various modifications may be made without departing from the spirit and scope of the invention. Accordingly, it is to be understood that the invention is not to be limited by the specific illustrated embodiment but only by the scope of the appended claims.

What is claimed is:

1. A spinal fusion device for adjusting the space between vertebrae comprising an upper section having a top surface and depending sidewalls, said sidewalls terminating in a first inclined plane, a lower section having a bottom surface and upstanding sidewalls, said upstanding sidewalls terminating in a second inclined plane, said first inclined plane and said second inclined plane being complementary to each other in movable contact, said upstanding sidewalls having a thickness, a portion of said upstanding sidewalls having a lesser thickness, a flange connected to said top surface, said flange adapted to contact said portion of said upstanding sidewalls having a lesser thickness and provide alignment of said upper section and said lower section, and a distractor located between said upstanding sidewalls, said distractor having adjustment means for moving said upper section relative to said lower section thereby increasing the distance between said top surface and said bottom surface.

2. A spinal fusion device for placement in the disk space between adjacent vertebrae comprising a hollow body having an upper section with a top surface for contacting one vertebra and a lower section with a bottom surface for contacting the adjacent vertebra, sidewalls depending from said top surface terminating in an inclined plane, upstanding sidewalls projecting from said bottom surface terminating in an inclined plane, said depending sidewalls and said upstanding sidewalls in sliding contact with each other along said inclined plane, said upstanding sidewalls having a thickness, a portion of said upstanding sidewalls having a lesser thickness, a flange connected to said top surface, said flange adapted to contact said portion of said upstanding sidewalls having a lesser thickness and provide alignment of said upper section and said lower section, whereby the distance between said bottom surface and said top surface is adjustable by moving said upper section relative to said lower section.

3. A spinal fusion device of claim 2 comprising an end wall depending from said top surface, said end wall including a means for moving said upper section relative to said lower section, a distractor adapted to be inserted in said hollow body and contact said upstanding sidewalls, a link connected to said distractor for connecting said means and said distractor to adjust said distance.

4. A spinal fusion device of claim 2 comprising a distractor adapted for insertion in said hollow body, said distractor having an end plate, said end plate of a size to contact said upstanding sidewalls, said end plate including a bore.

5. A spinal fusion device of claim 4 comprising a body connected to said end plate, said body having a bore for alignment with said end plate bore.

6. A spinal fusion device of claim 5 comprising an end wall depending from said top surface, said end wall including a means for moving said upper section relative to said lower section.

7. A spinal fusion device of claim 6 comprising a link extending through said end plate bore and said body bore and connected to said means for moving said upper section relative to said lower section, said link adapted to reduce the distance between said end plate and said end wall.

8. A spinal fusion device of claim 2 comprising a series of lands and grooves on said top surface for increasing purchase of said device.

9. A spinal fusion device of claim 2 comprising a series of lands and grooves on said bottom surface for increasing purchase of said device.

10. A spinal fusion device of claim 2 comprising a series of lands and grooves on said top surface and a series of lands and grooves on said bottom surface for increasing purchase of said device.

* * * * *